United States Patent [19]

Sullivan

[11] Patent Number: 4,903,718
[45] Date of Patent: Feb. 27, 1990

[54] FLEXIBLE ULTRASONIC CLEANING BAG
[75] Inventor: Jerry F. Sullivan, Ridgewood, N.J.
[73] Assignee: Ipco Corporation, White Plains, N.Y.
[21] Appl. No.: 259,926
[22] Filed: Oct. 19, 1988
[51] Int. Cl.4 ................................................ B08B 3/12
[52] U.S. Cl. ..................................... 134/184; 383/41; 383/43; 383/63
[58] Field of Search ..................... 134/1, 184; 206/601, 206/620; 383/41, 43, 63–67, 902, 904, 907; 68/3 SS; 366/127

[56] References Cited

U.S. PATENT DOCUMENTS

| | | | |
|---|---|---|---|
| 3,051,605 | 8/1962 | Stannard | 383/904 X |
| 3,208,640 | 9/1965 | Paulson | 383/41 X |
| 3,217,770 | 11/1965 | Garth | 206/620 X |
| 3,383,017 | 5/1968 | Krings | 383/907 X |
| 3,637,133 | 1/1972 | Doyen et al. | 383/67 |
| 3,802,919 | 4/1974 | Saffir | 383/63 X |
| 3,937,236 | 2/1976 | Runnells | 68/3 SS X |
| 3,965,953 | 6/1976 | Becker et al. | 383/41 X |
| 4,691,725 | 9/1987 | Parisi | 366/127 X |
| 4,707,389 | 11/1987 | Ward | 383/906 X |

FOREIGN PATENT DOCUMENTS 1371743 7/1964 France ............................. 383/907 X Primary Examiner—Philip R. Coe
Attorney, Agent, or Firm—Helfgott & Karas

[57] ABSTRACT

A container for cleaning dentures, dental or medical instruments, or the like is formed as a plastic bag which is filled with a cleaning solution and immersed together with dentures, instruments, or the like placed therein in a fluid of an ultrasonic cleaning device. The container is provided with an opening receiving the dentures, instruments, or the like and is sealingly closable by a closure such as a slide fastener. A number of such containers may be placed into a tray and immersed into the ultrasonic cleaning device, wherein the bags are subjected to ultrasonic vibrations transmitted to the cleaning solution inside the bags to thereby clean the articles in the bags.

26 Claims, 2 Drawing Sheets

FLEXIBLE ULTRASONIC CLEANING BAG

BACKGROUND OF THE INVENTION

The present invention relates to containers for retaining a cleaning liquid for cleaning dental or medical instruments, dentures, optical lenses, eyeglasses, or the like, specifically in ultrasonic cleaning devices, and to a method for ultrasonically cleaning such items.

Cleaning of dental and medical instruments by means of ultrasonic vibrations is well known. Normally such instruments are placed into beakers made of glass, which are in turn placed on a tray or plate and filled with a cleaning solution, such as a detergent or the like. The tray or plate is inserted into an ultrasonic container which contains a bath. The container is equipped with an ultrasonic transducer which agitates the bath in the container. The vibrations cause the glass beaker to vibrate which causes the cleaning solution to erosively clean dirt from the immersed instruments. Ultrasonic devices of the foregoing type have been known. One of them is disclosed in U.S. Pat. No. 3,937,236.

The problems with such otherwise satisfactory retaining beakers are that they can easily break, they should be regularly cleaned, and they require significant space in the ultrasonic container because the beakers should be spaced apart from each other. Additionally, specific holders to support the glass beakers must be provided within the ultrasonic container.

When it is desired to clean dentures, heretofore, the dentures are placed in a similar beaker and a special denture cleaning fluid is poured into the beaker. The beaker is then inserted in a holder in an ultrasonic cleaner. The ultrasonic cleaning device typically includes its own liquid bath which is utilized in the ultrasonic device as a load to prevent the ultrasonic device from harm should there not by any items being cleaned.

As in the case of dental or medical instruments the beaker for the dentures takes a lot of room, must constantly be cleaned, has a tendency to break, and the ultrasonic device can only hold one or two beakers since they must be supported in a holder.

Accordingly, there is need for a disposable container for the cleaning of dental or medical instruments, dentures, or the like, which can be used in conjunction with an ultrasonic device.

SUMMARY OF THE INVENTION

It is accordingly an object of the present invention to provide a disposable bag to be filled with a cleaning solution for the holding of dental or medical instruments, dentures, or the like to be subjected to ultrasonic vibrations.

It is another object of the invention to provide a cleaning solution retaining bag for receiving dental or medical instruments, dentures, or the like, and which does not require a great deal of space in an ultrasonic device.

Yet another object of the present invention is to provide a flexible container for dental or medical instruments, dentures, or the like subject to ultrasonic sterilizing, which is easy to use.

A further object of this invention is to provide a flexible container for dental or medical instruments, dentures, or the like to be cleaned, which is inexpensive and easy to manufacture.

Briefly, in accordance with the present invention, there is provided a container for dentures, dental or medical instruments, or other items to be subjected to ultrasonic cleaning. The container comprises a closed envelope-shaped flexible, soft pliable receptacle for receiving dentures or instruments. Inlet means are provided for admitting a cleaning solution into the receptacle. An openable lock is also provided permitting dentures or instruments into the receptacle and for closing the receptacle during the ultrasonic cleaning. An outlet means is available for discharging the cleaning solution from the receptacle.

In an embodiment, a slide fastener type of closure is provided near the top of the receptacle, which serves as an opening through which the dentures or instruments are inserted into the receptacle and which can then be closed. In an embodiment, the flexible receptacle is a plastic bag.

There is also provided a method of cleaning dentures, dental or medical instruments, or the like by placing them into a cleaning solution and subjecting them to ultrasonic vibrations. The method comprises providing at least one closable flexible soft plastic bag, placing dentures, instruments, or the like into the bag, filling the bag with a cleaning solution via an inlet provided on the bag, closing the bag, immersing the filled bag within a fluid bath of an ultrasonic cleaning device, subjecting the fluid bath and the filled bag immersed therein to ultrasonic vibrations which are transmitted to the cleaning solution to shake off and remove contaminated particles from the dentures, instruments, or the like, removing the bag from the fluid bath of the cleaning device and emptying the bag.

In an embodiment, an inlet valve and an outlet valve are provided on the plastic bag to fill the bag with the cleaning solution and to empty the bag, respectively.

In an embodiment, a single two-way valve is provided on the plastic bag for filling the bag with a cleaning solution and then, emptying the bag.

A tear-off tab on one of the bottom corners of the bag may be provided in an embodiment of the invention.

In accordance with the invention there is also provided a combination of the plastic bag with an ultrasonic cleaning device, a fine mesh-like tray is provided, into which a number of plastic bags, separated from each other, are placed. The tray is immersed into the container of the ultrasonic cleaning device wherein the tray and the bags are subjected to ultrasonic vibrations to clean the contents of the bags.

The aforementioned objects, features and advantages of the invention, will, in part, be pointed out with particularity, and will, in part, become obvious from the following more detailed description of the invention, taken in conjunction with the accompanying drawings, which form an integral part thereof.

DETAILED DESCRIPTION OF THE PREFERRED EMBODIMENTS

Figure 1:
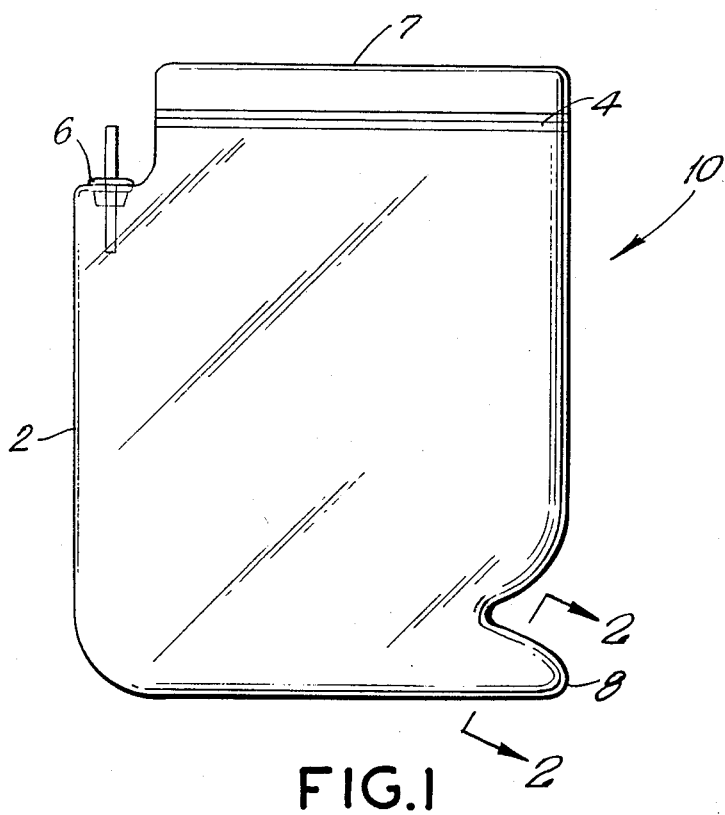
FIG. 1 is a side view of a disposable plastic bag for cleaning dental or medical instruments or dentures, according to one embodiment of the invention.
Figure 2:
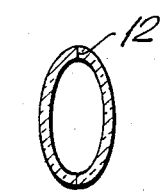
FIG. 2 is a sectional view taken along line 2—2 of FIG. 1.

As best seen in FIG. 1 a container or bag generally denoted at 10 includes a flexible, soft, pliable envelope-shaped receptacle or body 2 formed of plastic film, and a closure means 4 which slide fastener is shown as preferably a Zip-lock ® closure. The bag is filled by a user to place dental or medical instruments, dentures or the like (not shown) into the bag and then closed thereafter. A filling valve 6 is provided at the top of the flexible body or receptacle 2 of the bag to admit a cleaning solution into the bag.

In use, the dentures or instruments are inserted into the bag 10 which is typically initially dry. The top is closed. The valve 6 is used to inlet the cleaning liquid into the bag. The valve is shut off after the bag 10 has been filled. Thereafter the bag 10 is placed into a holder and immersed into the fluid of an ultrasonic cleaning apparatus or simply inserted directly into the liquid contained in the ultrasonic apparatus, as will be explained in detail below. After the dentures, instruments, or the like have been cleaned, bag 10 is removed from the ultrasonic device and its tear-off corner is cut off to permit the cleaning liquid to escape. In the case of instruments, the instruments can then be removed. When used to clean dentures, the bag can then be returned to the user and he can store the dentures in the bag and extract his dentures from the bag when he so desires.

Figure 3:
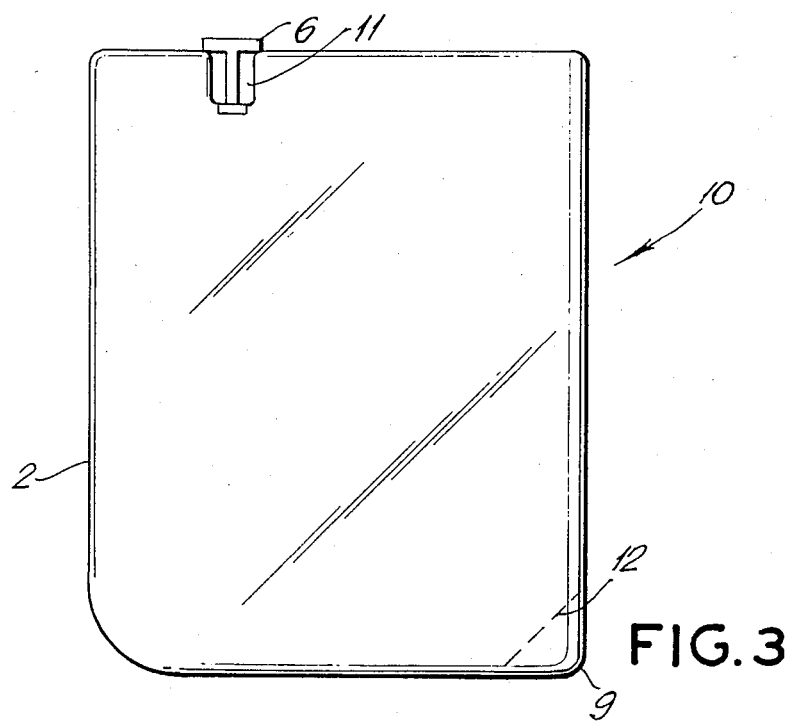
FIG. 3 is a side view of the plastic bag of another embodiment.

The tear-away tab 8 at the right-hand bottom corner may include a perforation or guide line 12 to aid the user to rip off the corner tab 8 to empty the bag after use. The perforation line 12 for cutting a bottom right-hand corner 9 of bag 10 is shown in FIG. 3.

Valve 6 can be a one-way valve for filling the bag or can be a two-way valve and thereby serve for discharging the cleaning liquid from the bag as well. Valve 6 in the embodiment of FIG. 3 is positioned in a recess or depression 11 formed in the upper wall of plastic bag 10.

A sheath of thermoplastic film may be used for making the bag according to the invention. The slide fastener 4 is provided on the top 7 of the opposing side walls of the bag. However, other types of closures can work as well.

Figure 5:
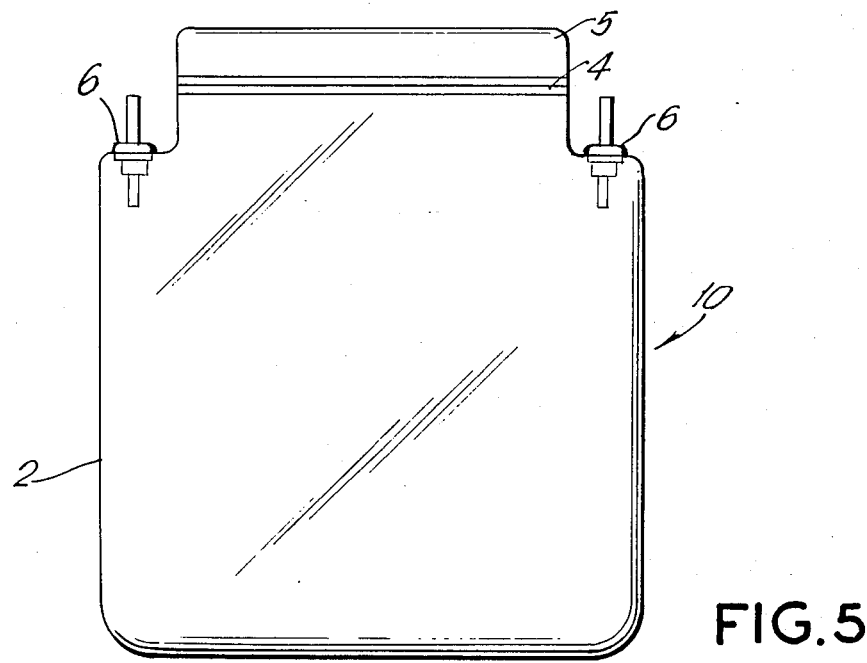
FIG. 5 is a side view of the ultrasonic cleaning bag of yet another embodiment of the invention.

In an embodiment shown in FIG. 5 two valves 6 and 16 are provided in the upper wall of the bag 10. If one of the valves is used for filling the bag with the cleaning liquid the other valve can be used for discharging the cleaning fluid from the bag. The aforedescribed bag is formed as an insulated system which prevents contamination of the articles placed therein and ensures a complete sterilization of those articles within the bag when filled with the cleaning fluid and subjected to ultrasonic vibrations.

Figure 4:
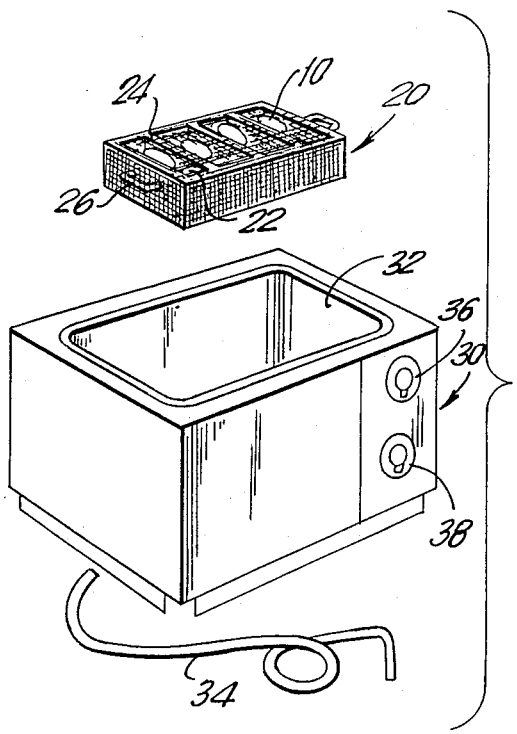
FIG. 4 is an exploded perspective view of the ultrasonic device with a tray supporting the bags of the present invention.

Referring now to FIG. 4 it will be seen that a number of pliable, plastic bags of the type described above can be placed into a perforated or fine mesh tray 20 which includes a plurality of compartments 22 each receiving an individual bag 10 and separated from each other by partitions 24. Depending on the size of the bags, a number of bags may be placed in each compartment 22 since the bags are soft and flexible and can be placed in the compartments adjacent to each other. Tray 20 has two handles 26 provided at two opposite side walls thereof. Any suitable holding rods or hooks may be attached to handles 26 to facilitate the immersion of tray 20 with bags 10 filled with the cleaning fluid and instruments or dentures and sealingly closed, into the bath of an ultrasonic device 30 or to suspend the tray from the upper edge of the container of the ultrasonic device 30 into its bath. It should be understood, that if the tops of the bag extend above the bath in the ultrasonic apparatus, the bag could remain open and yet avoid cross contamination.

The ultrasonic device 30 is of conventional type and includes a container 32, for example, of stainless steel for holding any suitable fluid, for example, water which serves as a coupling fluid to transmit ultrasonic vibrations to the cleaning fluid within each flexible bag 10. Container 32 has a drain outlet tube 34 and a cover (not shown) to sealingly close container 32 when the latter is in use.

The ultrasonic vibrations necessary to produce a cleaning action on the instruments or dentures disposed in the pliable plastic bags 10 are produced by a commonly known transducer and related electrical components, such as disclosed, for example, in U.S. Pat. Nos. 2,896,649 and 4,691,725. A voltage control knob 36 and a timer 38 to control ultrasonic vibrations in a known fashion are provided on the side wall of the ultrasonic device 30.

When tray 20 with bags 10 containing dentures, dental or medical instruments, or the like is lowered into the container 12 and electric power is applied to the transducer of the ultrasonic device in a known manner, the generated ultrasonic energy is propagated through the bath which fills container 12 and is transmitted through the vibrating tray and the walls of bags 10 to the cleaning liquid in the plastic bags.

Heretofore, glass beakers on other rigid containers were used to retain the instruments or dentures. Since the vibrations of the ultrasonic transducer had to be transmitted to the instruments, it was thought that only rigid containers would work satisfactorily. It might have been assumed that any soft or pliable material would dampen the vibrations. Surprisingly, the walls of plastic bags 10 do not dampen the ultrasonic vibrations produced in the bath which fills container 32 of the ultrasonic device and actually the walls of the bags vibrate. This permits the passage of such vibrations to the cleaning fluid contained in the bags when the latter are submerged in the bath of the container 32. The instruments and dentures are thus cleaned very satisfactorily without loss of efficiency. Nevertheless the problems of the rigid beakers are avoided. The bags can be stacked without breakage, can be pressed against each other to store more bags in the apparatus. Also, the bags can be disposable.

After the cleaning has been completed, the tray 20 with bags 10 is removed from the ultrasonic device 30. The dentures, instruments, or the like contained in bags 10 are completely cleaned and may be removed from the bags when desired.

Because soft pliable bags are used, the ultrasonic cleaner can now be used for numerous items, many of which could not previously have been handled. For example, contact lenses can now be cleaned by placing them in a small plastic bag with a cleaning solution in it. The bag is sealed and placed in the ultrasonic cleaning device. After cleaning, the solution is emitted by a hole or valve in the bag which is small enough to prevent the lenses from falling out. Likewise jewelry, eyeglasses or other articles can be cleaned using the plastic bags.

An ultrasonic device filled with a bag for cleaning other items can be used for processing plastic bags 10 filled with their own cleaning fluid and containing dentures or instruments. Dental tools in bags 10 can also be sterilized if a heater is provided to heat the fluid in the container of the ultrasonic device.

Plastic bags, e.g. Jiffy ® bags according to the invention can be filled with a cement removal solution or a denture cleaning solution or general cleaning fluid. A plurality of bags 10 simultaneously placed on the tray 20 can be each filled with a different solution and used for cleaning dentures or instruments, respectively. Some of such solutions can be harmful to each other and the provision of the separated or sealed plastic bags each for an individual solution offers the possibility of a simultaneous treatment of various items in different solutions with a total isolating of such solutions from each other.

Cleaning agent can be poured into bags 10 from a dispenser which may be provided with multiple bottles each having a pierceable cap. Alternatively, a dispenser may have a filling nozzle insertable into the valve opening of inlet valve 6. Dentures may be stored in such plastic bags.

While particular embodiments of the present invention have been shown and described, it will be obvious to those skilled in the art that changes and modifications may be made without departing from the invention in its broader aspects. Therefore, the aim in the appended claims is to cover all such changes and modifications as fall within the true spirit and scope of the invention. The matter set forth in the foregoing description and accompanying drawings is offered by way of illustration only and not as a limitation. The actual scope of the invention is intended to be defined in the following claims when viewed in their proper perspective based on the prior art.

What is claimed is:

1. A container for cleaning articles, such as dentures, dental or medical instruments, or the like, to be subjected to ultrasonic vibrations for cleaning, the container comprising:
   a flexible, soft, pliable receptacle for receiving articles to be cleaned and being capable of transmitting ultrasonic vibrations therethrough;
   inlet means for admitting a cleaning solution into said receptacle;
   openable lock means permitting said articles into said receptacle and for selectively closing said receptacle; and
   outlet means for discharging said cleaning solution for said receptacle, whereby said articles placed in the container filled with said solution and subjected to ultrasonic vibrations are cleaned in said container.

2. A container according to claim 1, wherein said receptacle is a plastic bag.

3. A container according to claim 2, wherein said plastic bag is sealed at a top thereof.

4. A container according to claim 1, wherein said lock means includes a slide fastener.

5. A container according to claim 4, wherein said slide fastener is provided on a side wall of said receptacle.

6. A container according to claim 1, wherein said inlet means includes a valve provided on said receptacle and operated to fill said receptacle with said cleaning solution.

7. A container according to claim 6, wherein said valve is a one-way valve.

8. A container according to claim 6, wherein said valve is a two-way valve.

9. A container according to claim 6, wherein said outlet means includes a further valve provided on said receptacle and operated to drain said cleaning solution from said receptacle.

10. A container according to claim 9, wherein said receptacle has two recessed portions at opposite sides thereof, said recessed portions accommodating said valve and said further valve, respectively.

11. A container according to claim 6, wherein said receptacle has a top wall formed with a depression, said valve being disposed in said depression.

12. A container according to claim 1, wherein said outlet means includes a tear-off tab at a bottom corner of said receptacle to drain the cleaning solution therefrom.

13. A container according to claim 1, wherein said outlet means includes a tear-off corner of said receptacle and provided with indication means to facilitate removal of said corner from said receptacle to drain the cleaning solution therefrom.

14. A container according to claim 1, wherein said outlet means includes an outlet valve provided on said receptacle and operated to drain the cleaning solution from said receptacle.

15. A container according to claim 1, and comprising an open top and closure means at said open top, said open top serving as said inlet means, outlet means and for permitting articles into said bag.

16. A container for dentures, dental instruments, or the like to be subjected to ultrasonic vibrations for cleaning, the container comprising:
   a closable envelope-shaped flexible, soft plastic bag for receiving dentures, instruments, or the like and being capable of transmitting ultrasonic vibrations therethrough;
   inlet means for admitting a cleaning solution into said bag;
   openable lock means permitting dentures, instruments, or the like into said receptacle and closing said bag; and
   outlet means for discharging said cleaning solution for said bag whereby dentures, instruments or the like placed in the container filled with said solution and subjected to ultrasonic vibrations are cleaned in said container without swishing the container.

17. A container according to claim 16, wherein said lock means includes a slide fastener.

18. A container according to claim 17, wherein said inlet means and said outlet means each includes a one-way valve.

19. A container for dentures, dental or medical instruments, or the like, to be subjected to ultrasonic vibrations for cleaning, the container comprising:
   an envelope-shaped flexible, soft plastic bag for receiving dentures, instruments, or the like and being capable of transmitting ultrasonic vibrations therethrough;
   an inlet valve provided on said bag for admitting a cleaning solution into said bag;
   a slide fastener having an openable mouth for admitting dentures, instruments, or the like into said bag and closable for closing said bag; and
   a tear-off tab provided on a corner of said bag and tearable to permit said cleaning solution to drain from said bag whereby dentures, instruments or the like placed in the container filled with said solution and subjected to ultrasonic vibrations are cleaned in said container without swishing the container.

20. In a combination of a container for dentures, dental or medical instruments, or the like to be subjected to ultrasonic vibration cleaning within an ultrasonic cleaning device including a fluid bath, the container comprising:
- a flexible soft pliable receptacle for receiving dentures, instruments, or the like;
- inlet means for admitting a cleaning solution into said receptacle;
- closure means which is opened to permit dentures, instruments, or the like into said receptacle and is closed to seal said receptacle; and
- outlet means for discharging said cleaning solution for said receptacle,
- said container receiving dentures, instruments, or the like and being filled with said cleaning solution and immersed into said fluid bath of said ultrasonic cleaning device, whereby ultrasonic vibrations induced in said fluid bath during operation of said ultrasonic cleaning device are transmitted through walls of said receptacle to said cleaning solution to remove contaminated particles from the dentures, instruments, or the like.

21. The combination according to claim 20, wherein said receptacle is a plastic bag.

22. The combination according to claim 21, and further comprising means for holding a plurality of containers to be immersed into said fluid bath of said ultrasonic cleaning device.

23. The combination according to claim 22, wherein said holding means comprises a tray including a mesh body having a plurality of compartments each receiving at least one of said containers, and handles provided on said body.

24. The combination according to claim 23, wherein said mesh body includes a plurality of partitions separating said compartments from each other.

25. The combination according to claim 22, wherein each of said containers is filled with a different cleaning solution.

26. The combination according to claim 20, wherein said container comprises an open top which serves as said inlet means and said outlet means, and wherein said closure means closes said open top.

* * * * *